United States Patent
Kang et al.

(10) Patent No.: US 9,057,594 B2
(45) Date of Patent: Jun. 16, 2015

(54) SAPPHIRE LENS-BASED OPTICAL FIBER PROBE FOR OPTICAL COHERENCE TOMOGRAPHY

(71) Applicant: The Johns Hopkins University, Baltimore, MD (US)

(72) Inventors: Jin U. Kang, Ellicott City, MD (US); Mingtao Zhao, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 200 days.

(21) Appl. No.: 13/709,984

(22) Filed: Dec. 10, 2012

(65) Prior Publication Data

US 2014/0160486 A1    Jun. 12, 2014

(51) Int. Cl.
  *G01B 9/02* (2006.01)
  *A61B 3/10* (2006.01)

(52) U.S. Cl.
  CPC .......... *G01B 9/0205* (2013.01); *G01B 9/02035* (2013.01); *G01B 9/02091* (2013.01); *A61B 3/102* (2013.01)

(58) Field of Classification Search
  CPC ...... G01B 9/02; A61B 5/0066; A61B 5/6852; A61B 5/0073; G01N 21/4795
  USPC .......................................................... 356/479
  See application file for complete search history.

(56) References Cited

U.S. PATENT DOCUMENTS

| | | | |
|---|---|---|---|
| 4,826,272 A * | 5/1989 | Pimpinella et al. | 385/92 |
| 5,010,886 A * | 4/1991 | Passafaro et al. | 600/439 |
| 5,688,261 A * | 11/1997 | Amirkhanian et al. | 606/17 |
| 7,344,528 B1 * | 3/2008 | Tu et al. | 606/7 |
| 2005/0254061 A1 * | 11/2005 | Alphonse | 356/479 |
| 2006/0103850 A1 * | 5/2006 | Alphonse et al. | 356/479 |
| 2007/0038123 A1 * | 2/2007 | Fulghum | 600/476 |
| 2010/0036279 A1 * | 2/2010 | Rieth | 600/551 |

FOREIGN PATENT DOCUMENTS

| | | |
|---|---|---|
| WO | WO-0111409 A2 | 2/2001 |
| WO | WO-2008137710 A1 | 11/2008 |
| WO | WO-2009039303 A1 | 3/2009 |
| WO | WO-2011050249 A1 | 4/2011 |
| WO | WO-2012018832 A2 | 2/2012 |

OTHER PUBLICATIONS

Han et al., "Common path optical coherence tomography with fibre bundle probe," Electronics Letters 45, 1110-1112 (2009).

(Continued)

*Primary Examiner* — Tarifur Chowdhury
*Assistant Examiner* — Md Rahman
(74) *Attorney, Agent, or Firm* — Venable LLP; Henry J. Daley; Laura G. Remus

(57) ABSTRACT

A probe for an optical coherence tomography system according to an embodiment of the current invention includes a sheath having a proximal end and a distal end and defining a lumen therein, an optical fiber disposed at least partially within the lumen of said sheath, and a sapphire lens attached to the distal end of the sheath to form a fluid-tight seal to prevent fluid from entering the lumen of said sheath. The optical fiber has an end arranged in an optical path with the sapphire lens to provide optical coupling between the sapphire lens and the optical fiber.

19 Claims, 5 Drawing Sheets

(56) References Cited

OTHER PUBLICATIONS

Kang et al., "Common-path Optical Coherence Tomography for Biomedical Imaging and Sensing," J. Opt. Soc. Korea 14, 1-13 (Mar. 2010).

Tan et al., "In-fiber common-path optical coherence tomography using a conical-tip fiber," Opt. Express 17, 2375-2384 (2009).

Benalcazar et al., "Aberration characterization for the optimal design of high-resolution endoscopic optical coherence tomography catheters," Opt. Lett. 37, 3 (Mar. 2012).

Choma et al., "Sensitivity advantage of swept source and Fourier domain optical coherence tomography," Opt. Express 11, 7 (2003).

d. Boer et al., "Improved signal-to-noise ratio in spectral-domain compared with time-domain optical coherence tomography," Opt. Lett. 28, 3 (2003).

Fercher et al., "Measurement of intraocular distances by backscattering spectral interferometry," Opt. Commun. 17, 6 (1995).

Huang et al., "Optical coherence tomography," Science 254, 4 (1991).

Kang et al., "Endoscopic Functional Fourier Domain Common-Path Optical Coherence Tomography for Microsurgery," IEEE J. of Select. Topic in Quantum. Electron. 16, 12 (Jul./Aug. 2010).

Leitgeb et al., "Performance of fourier domain vs. time domain optical coherence tomography," Opt .Express 11, 6 (2003).

Li et al., "Intraluminal fiber-optic Doppler imaging catheter for structural and functional optical coherence tomography," Opt. Lett. 26, 3 (2001).

Mao et al., "Graded-index fiber lens proposed for ultrasmall probes used in biomedical imaging," Appl. Opt 46, 8 (2008).

McLaughlin et al., "Imaging of Breast Cancer With Optical Coherence Tomography Needle Probes: Feasibility and Initial Results " IEEE J. Sel. Topics Quantum Electron. 18, 8 (May/Jun. 2012).

Tearney et al., "In vivo endoscopic optical biopsy with optical coherence tomography," Science 276, 3 (1997).

Yamanari et al., "Fiber-based polarization-sensitive Fourier domain optical coherence tomography using B-scan-oriented polarization modulation method," Opt. Express 14, 6502 (2006).

Yang et al., "Interstitial Doppler optical coherence tomography," Opt.Lett. 30, 3 (2005).

Yun et al., "High-speed optical frequency-domain imaging," Opt. Express 11, 11 (2003).

Zawadzki et al., "Adaptive-optics optical coherence tomography for high-resolution and highspeed 3D retinal in vivo imaging," Opt. Express 13, 15 (2005).

Zhao et al., "Single camera sequential scan based polarization sensitive SDOCT for retinal imaging," Opt.Lett. 34, 3 (2009).

Zhu et al., "Design and validation of an angle-resolved low-coherence interferometry fiber probe for in vivo clinical measurements of depth-resolved nuclear morphology," J.Biomed. Opt. 16(Jan. 2011).

Li et al., "Signal-to-noise ratio analysis of all-fiber common-path optical coherence tomography," Applied Optics, 2008, vol. 47, No. 27, pp. 4833-4840.

Lorenser et al., "Ultrathin side-viewing needle probe for optical coherence tomography," Optics Letters, vol. 36., No. 19, 2011, pp. 3894-3896.

\* cited by examiner

SAPPHIRE LENS-BASED OPTICAL FIBER PROBE FOR OPTICAL COHERENCE TOMOGRAPHY

This invention was made with Government support of Grant No. R01 EY021540, awarded by the Department of Health and Human Services, The National Institutes of Health (NIH). The U.S. Government has certain rights in this invention.

BACKGROUND

1. Field of Invention

The field of the currently claimed embodiments of this invention relates to optical coherence tomography (OCT) systems, and more particularly to sapphire lens-based optical fiber probes for OCT systems and OCT systems that incorporate the probes.

2. Discussion of Related Art

Optical coherence tomography (OCT) is being widely used for non-destructive, cross-sectional imaging of biological tissues [1-6]. A single-mode fiber can be lensed with state-of-the-art micro-optics to form an imaging beam with a spot size around a few μm in gastrointestinal endoscopy, coronary artery imaging, and needle-based Doppler OCT. The commonly used lensing components in fiber-optic microprobes are gradient-index (GRIN) lenses [7,], drum lenses [9], fiber fused ball lenses [10], and special liquid-forming ball lenses. For retina vitrectomy surgery, we have been developing a handheld compact forward sensing and imaging probe attached to surgical tool tips to detect the distance between the tool tips and critical areas of the retina, so they can avoid scratching healthy retina surfaces. The GRIN lens-based common-path (CP) probe has only led to sensitivity up to 44 dB in SDOCT. Although fused ball lenses demonstrated impressive performance in non-CP Doppler OCT, several main drawbacks of fused lenses are lower refractive index (n=1.48), teardrop (non-spherical shape), limited diameter (generally less than 500 μm), and they are fragile—which prevents the imaging lens from being directly exposed to tissue. There thus remains a need for improved probes for OCT systems, and OCT systems that incorporate the probes.

SUMMARY

A probe for an optical coherence tomography system according to an embodiment of the current invention includes a sheath having a proximal end and a distal end and defining a lumen therein, an optical fiber disposed at least partially within the lumen of said sheath, and a sapphire lens attached to the distal end of the sheath to form a fluid-tight seal to prevent fluid from entering the lumen of said sheath. The optical fiber has an end arranged in an optical path with the sapphire lens to provide optical coupling between the sapphire lens and the optical fiber.

An optical coherence tomography system according to an embodiment of the current invention includes a fiber-optic sensor system, a light source optically coupled to the fiber-optic sensor system, and a detection system optically coupled to the fiber-optic sensor system. The fiber-optic sensor system includes an optical probe. The optical probe includes a sheath having a proximal end and a distal end and defining a lumen therein, an optical fiber disposed at least partially within the lumen of said sheath, and a sapphire lens attached to the distal end of the sheath to form a fluid-tight seal to prevent fluid from entering the lumen of said sheath. The optical fiber has an end arranged in an optical path with the sapphire lens to provide optical coupling between the sapphire lens and the optical fiber.

BRIEF DESCRIPTION OF THE DRAWINGS

Further objectives and advantages will become apparent from a consideration of the description, drawings, and examples.

DETAILED DESCRIPTION

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "light" as used herein is intended to have a broad meaning that can include both visible and non-visible regions of the electromagnetic spectrum. For example, visible, near infrared, infrared and ultraviolet light are all considered as being within the broad definition of the term "light."

An embodiment of the current invention provides a novel sapphire ball lens-based fiber-optic CP-OCT probe applicable for intraocular imaging without dispersion and complex conjugate issue, with sensitivity up to 88 dB. The sapphire ball lens has excellent optical-imaging quality and a high refractive index of 1.75—which could improve lateral resolution and increase focusing power. The higher index enables the probe to function even when it is submerged in the vitreous gel. This can save the protective sheath or sealed optical window to simplify the probe design and fabrication to minimize its dimension. The relatively perfect spherical shape of the sapphire lenses also reduces the astigmatism and partial coma which generally occurs in fused ball lenses. In addition, a theoretical sensitivity model of CP-OCT was derived and shows that the sensitivity of our probe is up to 88 dB—approaching the theoretical limitation of CP-OCT—which is significantly higher than a recently reported CP-SDOCT probe based on GRIN lens sensitivity of 44 dB [11]. Two 25-gauge prototype common-path fiber probes have been developed. One with lateral resolution of 11 μm was demonstrated for bovine corneal and retinal imaging ex vivo in air and in vitreous gel.

Figure 1:
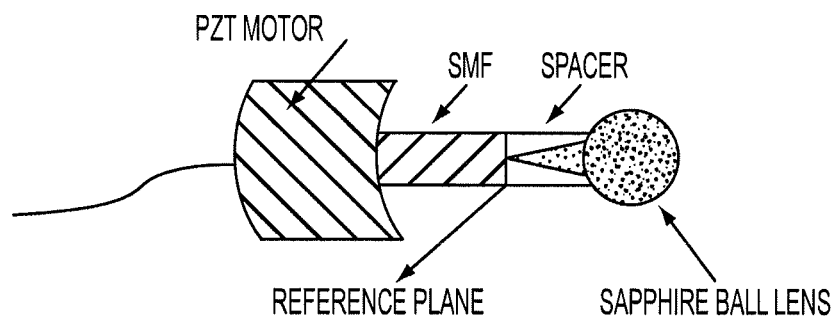
FIG. 1 is a schematic illustration of a probe for an optical coherence tomography system according to an embodiment of the current invention.

FIG. 1 provides a schematic illustration of a probe for an optical coherence tomography system according to an embodiment of the current invention. The probe of FIG. 1 includes a sheath having a proximal end and a distal end and defining a lumen therein, an optical fiber (SMF) disposed at least partially within the lumen of the sheath, and a sapphire lens attached to the distal end of the sheath to form a fluid-tight seal to prevent fluid from entering the lumen of the sheath. The optical fiber has an end arranged in an optical path with the sapphire lens to provide optical coupling between the sapphire lens and the optical fiber. The optical fiber can be a single-mode optical fiber (SMF) at an operation wavelength of the optical coherence tomography system. In some embodiments, the sapphire lens can be a substantially spherical sapphire ball lens. However, in other embodiments the sapphire lens can be a partially spherical sapphire ball lens. Furthermore, a sapphire lens that has smooth curved surfaces can be attached to the sheath, and that has sufficient optical properties can be used in alternative embodiments. A substantially spherical sapphire ball lens is suitable for many applications. The term "substantially" means within the limits of manufacturing tolerance and/or within the tolerances required for the specific task.

The end of the optical fiber can be fixed within the lumen of the sheath to maintain a predetermined distance from the sapphire lens with a space reserved therebetween. In some embodiments, the space can be substantially a vacuum. In some embodiments, the space can be filled with a material that has a smaller refractive index than the optical fiber such that said end of the optical fiber reflects a portion of illumination light to provide a reference beam to be mixed with received light. The end of the optical fiber acts as a reference plane in such embodiments, as is illustrated in FIG. 1. The material can be a solid in some embodiments. For example, but not limited to, epoxy. In some embodiments, the material can be a gas. The term a gas is intended to include mixtures of gases and is intended to be broad enough to include air.

Figure 2B:
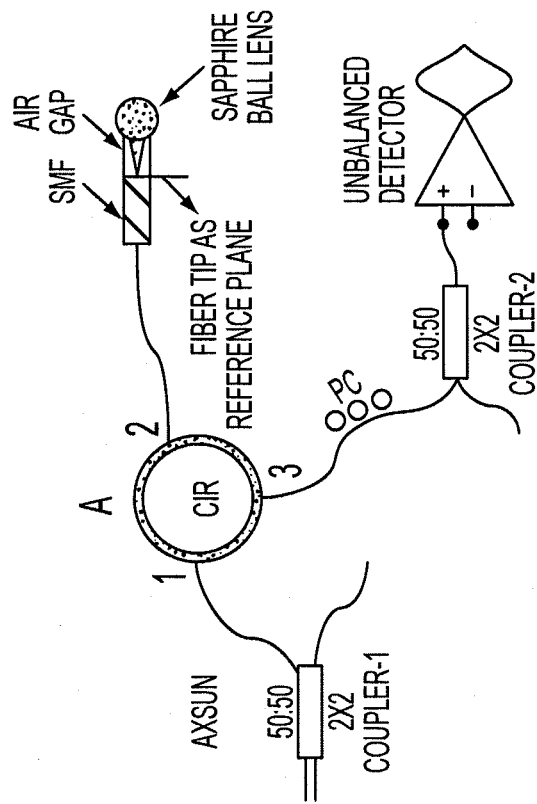
FIG. 2B shows an example of a lensed probe used for forward viewing in retina vitrectomy surgery according to an embodiment of the current invention. The probe can be attached to the minute surgical forceps.
Figure 2A:
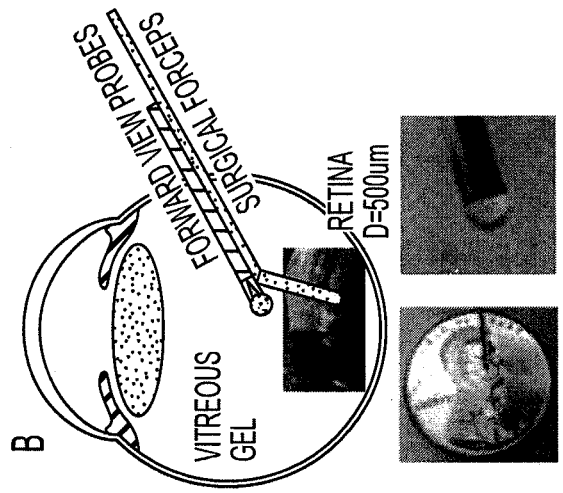
FIG. 2A is a schematic illustration of a CP-SSOCT system including a lensed probe that is compatible with a dual-arm configuration according to an embodiment of the current invention. The fiber tip functions as a reference plane and there can be an air gap or UV epoxy between fiber tip and ball lens as spacer.
Figure 3:
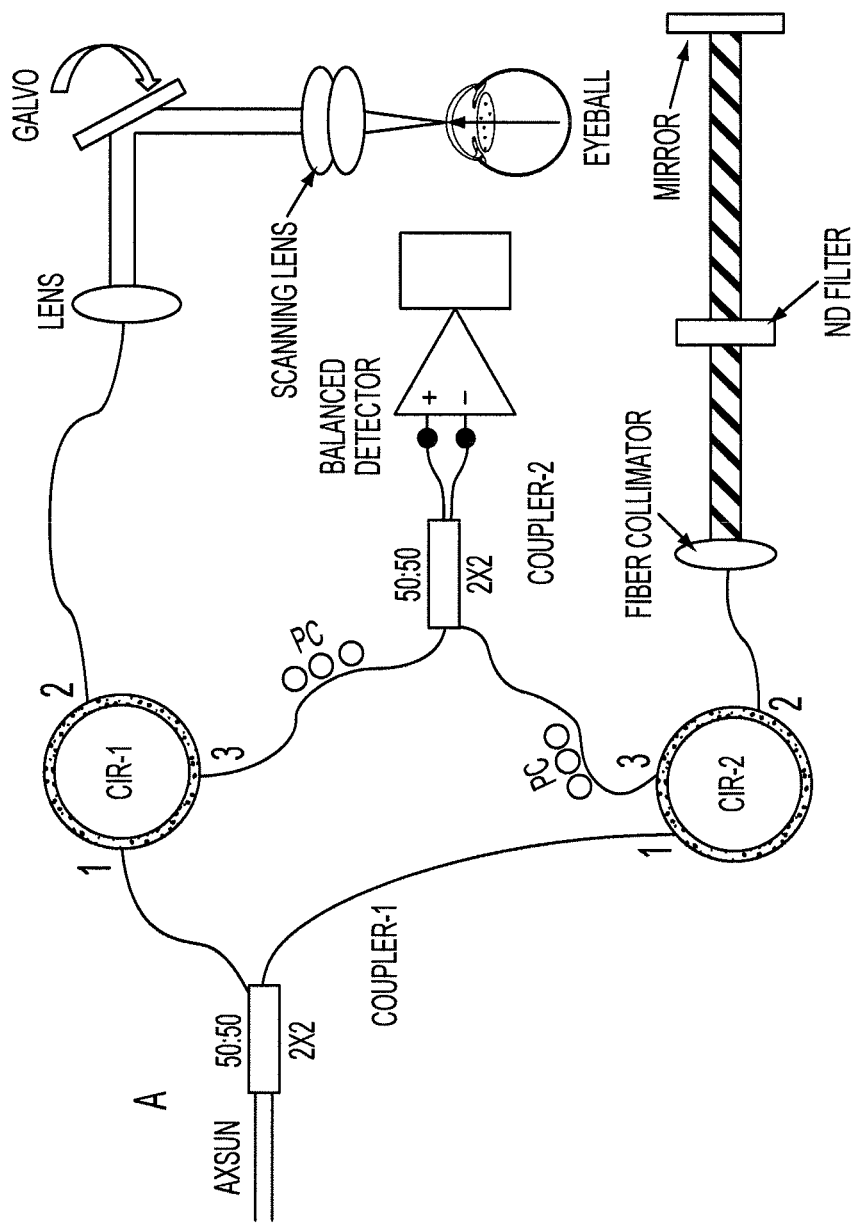
FIG. 3 is a schematic illustration of an OCT system used in the experiments.

Probes according to some embodiments of the current invention can be incorporated into OCT systems, as is illustrated in the examples of FIGS. 2A, 2B and 3. Such OCT systems can be, but are not limited to, common path OCT systems (CP-OCT systems). FIG. 1 shows the probe used with a PZT motor in that example. Optical probes according to some embodiments of the current invention can be attachable and removable from the fiber-optic sensor system. This can facilitate changing probes for different functions, such as, but not limited to changing while in use. This can also allow the probes to be disposable and/or cleanable. For example, they may be constructed of materials that permit autoclaving.

Further additional concepts and embodiments of the current invention will be described by way of the following examples. However, the broad concepts of the current invention are not limited to these particular examples.

EXAMPLES

Customized Gaussian beam paraxial ray ABCD matrix simulation [12] shows that working distances (WDs) vary with the diameter of the ball lens, wavelengths, and length and type of beam-expanding spacer. Generally, WD at a fixed wavelength is proportional to the diameter of the sapphire ball lens and wavelength. We fabricated two probes in-house to validate the simulation. They were assembled with a single-mode fiber (SMF-28) and a standard 25-gauge hypodermic needle. First, a section of air gap or UV epoxy spacer with refractive index of 1.51 was added between the single-mode fiber distal tip and a sapphire lens with a diameter of 500 μm. Then the air gap or UV epoxy gap were adjusted properly to achieve designed working distance. The reference power is from the fiber distal tip. The WDs were experimentally obtained from the sensitivity falling off of two probes. The parameters of two designs are listed in Table 1.

TABLE 1

Design parameters of two probes (all units in μm)

| Spacer/Length | Theoretical WD | Experimental WD | DOF/Spot size |
|---|---|---|---|
| Air/275 | 390 | 415 ± 5 | 151/11 |
| UV/169 | 1197 | 1221 ± 15 | 1478/18 |

To the best of our knowledge, no CP-OCT probes have been reported to reach sensitivity up to 88 dB [13]. A dual-balanced detector cannot be used for CP-OCT configurations since it will reject the CP-OCT signal and other common-mode optical noises. To estimate the optimum performance of CP-OCT with an unbalanced detector, we derived the sensitivity model of CP-OCT by modifying the analysis in prior studies [14-17]. The time-averaged signal power in single port of unbalanced detector of CP-OCT can be expressed as $$\langle i_s^2(t) \rangle = \left(\frac{\eta e}{hf}\right)^2 P_r P_s$$

Here, $P_r$ and $P_s$ denote the reference and signal power individually; $\eta$ is quantum efficiency, e is electron charge, h is Plank's constant. The noise power of a single detector contributed by total noises is given as $$\langle i_n^2(t) \rangle = \left[\frac{4kT}{R} + \frac{2\eta e^2}{hf} * \left(\frac{P_r}{2} + \frac{P_s}{2}\right) + \left(\frac{\eta e}{hf}\right)^2 * RIN * \left(\zeta * \left(\left(\frac{P_r}{2}\right)^2 + \left(\frac{P_s}{2}\right)^2\right) + \frac{P_r P_s}{2}\right)\right] * BW$$

where $$4\frac{kT}{R}$$

represents thermal noise and the second term is shot noise. The third terms include RN (relative intensity noise) noise induced by self-beating and cross-beating noises. ζ is called the common-mode rejection ratio, which is 0 dB for common-path OCT and typically −35 dB for balanced detector; BW is the bandwidth. Therefore, the sensitivity of the CP-OCT in dB can be expressed as $$\text{Sensitivity} = 10\log\left(\frac{i_s^2(t)}{i_n^2(t)}\right)$$

To verify the theoretical sensitivity analysis of CP-OCT, we implemented a CP-SSOCT, which is fully compatible with the dual-arm configuration of SSOCT. Probes with similar design can also be used for SDOCT as long as we change the type of single-mode fiber used. The reference plane of the probe radiated at the distal end of the single-mode fiber (SMF) was encased within a 25-gauge hypodermic needle and capped with a sapphire ball lens, facilitating its applications in liquid environments. We used a 1310-nm swept source laser with a wide tuning range of 100 nm (Axsun Technologies, Inc.) as the OCT engine, operating at a 50 kHz repetition rate with an axial resolution of 19 μm. Only the positive input port of a dual-balanced detector was used to collect the signal in CP-SSOCT. We used the following experimental parameters for sensitivity measurement: $P_s$=0.7 μw, $$4\frac{kT}{R} = 4.84\frac{pA^2}{Hz},$$

ζ=1 (0 dB), B=50 MHz and RIN=2.54*10$^{-14}$/Hz (−135.9 dB/Hz) which was the value at 25 MHz obtained using a spectrum analyzer. We used an equivalent ND filter of 37.5 dB to measure the sensitivity. The experimental sensitivity of the probe (data points with error bars) was compared to theoretical prediction of CP-SSOCT in FIG. 4 (lower curve).

Figure 4:
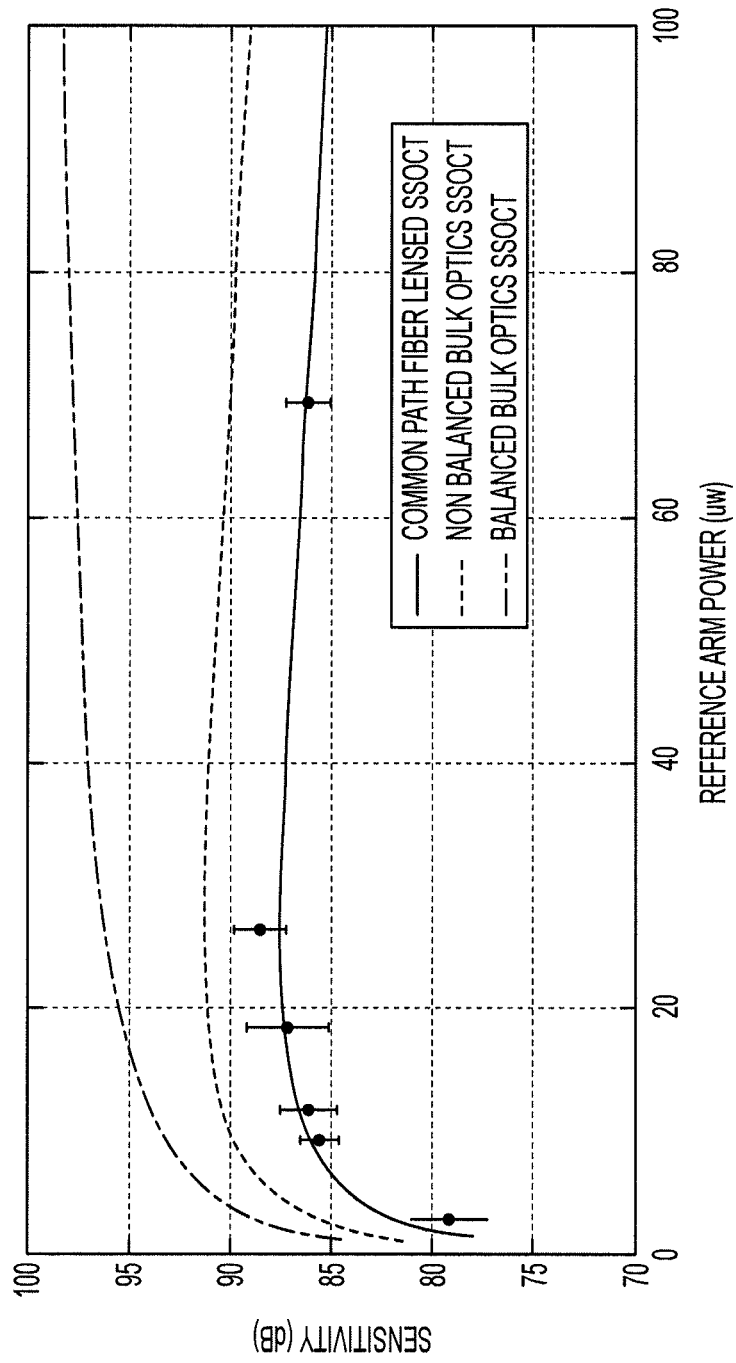
FIG. 4 shows theoretical sensitivity and experimental results. Theoretical sensitivity of a CP-SSOCT probe (bottom curve) with backward optical coupling efficiency of 40%; experimental results are data points with error bars; CP-SSOCT with backward coupling efficiency of 86.5% ($1/e^2$ width) is the center curve; traditional dual-balanced dual-arm bulky imaging head SSOCT with backward coupling efficiency of 86.5% is the tope curve.

The theoretical sensitivity plot of CP-SSOCT in FIG. 4 (lower curve) represents experimentally measured coupling efficiency of 40% which is mainly due to limited effective NA determined by the diameter of ball lens and the distance between fiber distal tip and ball lens center and immersed media. The experimental sensitivity agrees very well with the theoretical sensitivity of the CP-OCT and it is only 8 dB less than the dual-arm bulky imaging head SSOCT when reference arm power is around 20 μW. (The legend inserted in FIG. 4 labels the curves in the reverse order that they appear in the graph.) The optimal sensitivity is around 88 dB when the reference arm power is between 19 μW and 25 μW. The best sensitivity that CP-SSOCT can achieve is only around 3-4 dB lower than that of traditional dual-arm SSOCT, provided the probe's coupling efficiency increases to 86.5%. Compared to common path time domain OCT, common-path SSOCT and SDOCT probes could theoretically improve the sensitivity by a factor of N, which is the sampling point in SSOCT and the total dispersed photodetector elements of a camera in SDOCT. The probe having an air gap with WD of 415 μm is preferable for biological imaging due to better lateral resolution of 11 μm. Another probe—using UV epoxy as spacer—is optimal for distance sensing due to its long WD and depth of field.

Figures 5A, 5B, 5C, 5D, 5E, 5F:
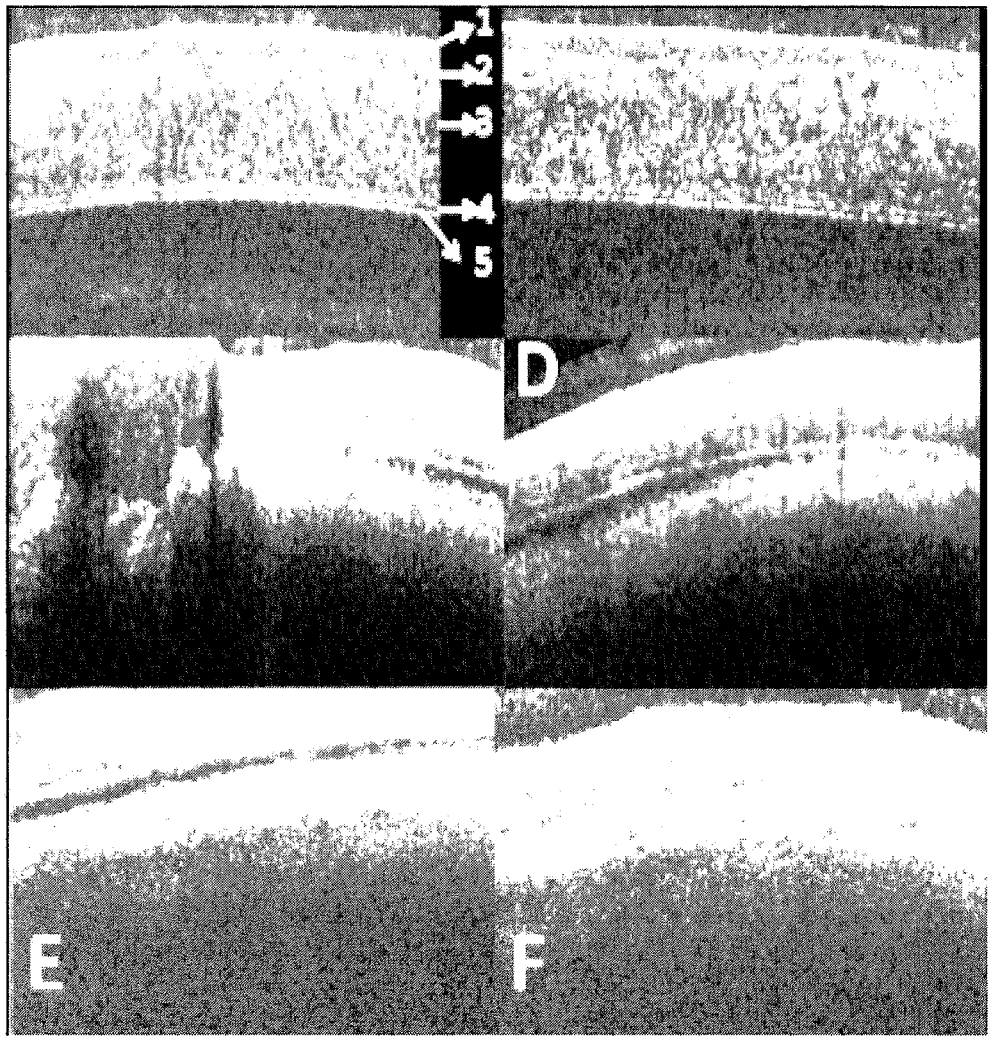
FIGS. 5A-5F show results for a cow's cornea and retina images (H 2.75 mm by V 2.1 mm) A, Cornea image. We can clearly identify the following five layers: epithelium (1), Bowman's layer (2), stroma (3), Descemet's membrane, (4), and endothelium (5). B, Corneal image far away from the apex. C is the OCT cross-sectional image of optical nerve head. D is away from the optical nerve head and shows clear layer structures of retina. E and F were captured when the probe was immersed in vitreous gel with a length of 32 mm. All images did not have frame average.

We performed bovine cornea and retina imaging ex vivo both in air and in vitreous gel to assess the probe's performance. The cornea images of FIGS. 5A and 5B were captured by manually scanning the probe tip in air. The sapphire ball lens keeps a distance of 300 μm from the corneal apex and around 400 μm at the periphery of the cornea in FIG. 5A. Five corneal layers—epithelium, Bowman's layer, stroma, Descemet's membrane, and endothelium—were clearly resolved without any special post-processing. FIG. 5B was obtained at a lateral distance more than 2 mm from the apex. The endothelium layer can still be resolved even at a relatively large incident angle. FIG. 5C was illustrated by manually scanning the probe across the optical nerve head (ONH). Owing to the protected reference plane inside the needle, the left part of FIG. 5C can still be clearly imaged even when the probe is in contact with the tissue. The cross-sectional image far away from the nerve head was also displayed in FIG. 5D, which clearly shows the retinal layer structures. To mimic the clinical environment, the probe was inserted into the vitreous sack of a 34-mm diameter bovine eyeball for imaging and sensing. Considering that the probe was immersed in vitreous gel and that the vitreous gel has high viscosity, the acquired images, as shown in FIGS. 5E and 5F shows a notable image quality. These two figures clearly show the retinal layer structures which shows that the probe functions even when submerged in liquid. The dark dots in choroid area of FIG. 5F are hollow blood vessels. Some retina layers were already degenerated since the images were taken approximately 2 hours after the animal was sacrificed.

To conclude, we demonstrated a novel sapphire ball-lens probe for endoscopic biological tissue imaging. This is the first demonstration of a sapphire ball lens-based common-path OCT probe capable of imaging in the vitreous gel with a sensitivity up to 88 dB, approaching the theoretical limitation of CP-OCT. Its performance is significantly better than that of GRIN lens or glass ball legs-based CP-SDOCT. This device can be a valuable imaging and sensing tool for ophthalmology, gastrointestinal endoscopy, vascular systems, and brain plaque imaging, for example, and it could potentially substitute a bulk imaging head in some applications. A large diameter sapphire lens around 1 mm can be chosen to improve its working distance and resolution. The reflection artifacts of the ball lens can be removed with a proper anti-reflection (AR) coating.

REFERENCES

1. D. Huang, E. A. Swanson, C. P. Lin, J. S. Schuman, W. G. Stinson, W. Chang, M. R. Hee, T. Flotte, K. Gregory, C. A. Puliafito, and J. G. Fujimoto, "Optical coherence tomography," Science 254, 4 (1991).
2. A. F. Fercher, C. K. Hitzenberger, G. Kamp, and S. Y. El-Zaiat, "Measurement of intraocular distances by back-scattering spectral interferometry," Opt. Commun. 17, 6 (1995).
3. G. J. Tearney, M. E. Brezinski, B. E. Bouma, S. A. Boppart, C. Pitris, J. F. Southern, and J. G. Fujimoto, "In vivo endoscopic optical biopsy with optical coherence tomography," Science 276, 3 (1997).
4. M. Yamanari, S. Makita, V. D. Madjarova, T. Yatagai, and Y. Yasuno, "Fiber-based polarization-sensitive Fourier domain optical coherence tomography using B-scan-oriented polarization modulation method," Opt. Express 14, 6502 (2006).
5. M. Zhao and J. A. Izatt, "Single camera sequential scan based polarization sensitive SDOCT for retinal imaging," Opt. Lett. 34, 3 (2009).
6. R. Zawadzki, J. Steven, 0. Scot, M. Zhao, B. Bradley, J. A. Izatt, S. Choi, S. Laut, and J. Werner, "Adaptive-optics optical coherence tomography for high-resolution and high-speed 3D retinal in vivo imaging," Opt. Express 13, 15 (2005).

7. W. A. Benalcazar, W. Jung, and S. A. Boppart, "Aberration characterization for the optimal design of high-resolution endoscopic optical coherence tomography catheters," Opt. Lett. 37, 3 (2012).
8. X. Li, T. H. Ko, and J. G. Fujimoto, "Intraluminal fiber-optic Doppler imaging catheter for structural and functional optical coherence tomography," Opt. Lett. 26, 3 (2001).
9. Y. Zhu, N. G. Terry, J. T. Woosley, N. J. Shaheen, and A. Wax, "Design and validation of an angle-resolved low-coherence interferometry fiber probe for in vivo clinical measurements of depth-resolved nuclear morphology," J. Biomed. Opt. 16(2011).
10. V. X. D. Yang, Y. X. Mao, N. Munce, B. Standish, W. Kucharczyk, N. E. Marcon, B. C. Wilson, and I. A. Vitkin, "Interstitial Doppler optical coherence tomography," Opt. Lett. 30, 3 (2005).
11. R. A. McLaughlin, B. C. Quirk, A. Curatolo, R. W. Kirk, L. Scolaro, D. Lorenser, P. D. Robbins, B. A. Wood, C. M. Saunders, and D. D. Sampson, "Imaging of Breast Cancer With Optical Coherence Tomography Needle Probes: Feasibility and Initial Results" IEEE J. Sel. Topics Quantum Electron. 18, 8 (2012).
12. Y. Mao, S. Chang, S. Sherif, and C. Flueraru, "Graded-index fiber lens proposed for ultrasmall probes used in biomedical imaging," Appl. Opt 46, 8 (2008).
13. J. U. Kang, J.- H. Han, X. Liu, K. Zhang, C. G. Song, and P. Gehlbach, "Endoscopic Functional Fourier Domain Common-Path Optical Coherence Tomography for Microsurgery," IEEE J. of Select. Topic in Quantum. Electron. 16, 12 (2010).
14. R. Leitgeb, C. K. Hitzenberger, and A. F. Fercher, "Performance of fourier domain vs. time domain optical coherence tomography," Opt. Express 11, 6 (2003).
15. J. F. d. Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 3 (2003).
16. M. A. Choma, M. V. Sarunic, C. Yang, and J. A. Izatt, "Sensitivity advantage of swept source and Fourier domain optical coherence tomography," Opt. Express 11, 7 (2003).
17. S. H. Yun, G. J. Tearney, J. F. d. Boer, N. Iftimia, and B. E. Bouma, "High-speed optical frequency-domain imaging," Opt. Express 11, 11 (2003).

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:

1. A probe for an optical coherence tomography system, comprising:
    a sheath having a proximal end and a distal end, said sheath defining a lumen therein;
    an optical fiber disposed at least partially within said lumen of said sheath; and
    a sapphire lens attached to said distal end of said sheath to form a fluid-tight seal to prevent fluid from entering said lumen of said sheath,
    wherein said optical fiber has an end arranged in an optical path with said sapphire lens to provide optical coupling between said sapphire lens and said optical fiber,
    wherein said end of said optical fiber is fixed within said lumen to maintain a predetermined distance from said sapphire lens with a space reserved therebetween, and
    wherein said space is filled with a material that has a smaller refractive index than said optical fiber such that said end of said optical fiber reflects a portion of illumination light to provide a reference beam to be mixed with received light, said optical coherence tomography system being a common path optical coherence tomography system.

2. A probe for an optical coherence tomography system according to claim 1, wherein said optical fiber is a single-mode optical fiber at an operation wavelength of said optical coherence tomography system.

3. A probe for an optical coherence tomography system according to claim 1, wherein said sapphire lens is a substantially spherical sapphire ball lens.

4. A probe for an optical coherence tomography system according to claim 1, wherein said sapphire lens is a partially spherical sapphire ball lens.

5. A probe for an optical coherence tomography system according to claim 1, wherein said material is a solid.

6. A probe for an optical coherence tomography system according to claim 1, wherein said material is a gas.

7. A probe for an optical coherence tomography system according to claim 6, wherein said gas is air.

8. A probe for an optical coherence tomography system, comprising:
    a sheath having a proximal end and a distal end, said sheath defining a lumen therein;
    an optical fiber disposed at least partially within said lumen of said sheath; and
    a sapphire lens attached to said distal end of said sheath to form a fluid-tight seal to prevent fluid from entering said lumen of said sheath,
    wherein said optical fiber has an end arranged in an optical path with said sapphire lens to provide optical coupling between said sapphire lens and said optical fiber,
    wherein said end of said optical fiber is fixed within said lumen to maintain a predetermined distance from said sapphire lens with a space reserved therebetween, and
    wherein said space is substantially a vacuum such that said end of said optical fiber reflects a portion of illumination light to provide a reference beam to be mixed with received light, said optical coherence tomography system being a common path optical coherence tomography system.

9. An optical coherence tomography system, comprising:
    a fiber-optic sensor system;
    a light source optically coupled to said fiber-optic sensor system; and
    a detection system optically coupled to said fiber-optic sensor system,
    wherein said fiber-optic sensor system comprises an optical probe, comprising:
    a sheath having a proximal end and a distal end, said sheath defining a lumen therein,
    an optical fiber disposed at least partially within said lumen of said sheath, and
    a sapphire lens attached to said distal end of said sheath to form a fluid-tight seal to prevent fluid from entering said lumen of said sheath, wherein said optical fiber has an end arranged in an optical path with said sapphire lens to provide optical coupling between said sapphire lens and said optical fiber, wherein said end of said optical fiber is fixed within said lumen to maintain a predetermined distance from said sapphire lens with a space reserved therebetween, and wherein said space is filled with a material that has a smaller refractive index than said optical fiber such that said end of said optical fiber reflects a portion of illumination light to provide a reference beam to be mixed with received light, said optical coherence tomography system being a common path optical coherence tomography system.

10. An optical coherence tomography system according to claim 9, wherein said optical fiber is a single-mode optical fiber at an operation wavelength of said optical coherence tomography system.

11. An optical coherence tomography system according to claim 9, wherein said sapphire lens is a substantially spherical sapphire lens.

12. An optical coherence tomography system according to claim 9, wherein said sapphire lens is a partially spherical sapphire ball lens.

13. An optical coherence tomography system according to claim 9, wherein said fiber-optic sensor system comprises a sensing arm and a reference arm, said optical probe being at least a portion of said sensing arm.

14. An optical coherence tomography system according to claim 9, wherein said material is a solid.

15. An optical coherence tomography system according to claim 11, wherein said material is a gas.

16. An optical coherence tomography system according to claim 15, wherein said gas is air.

17. An optical coherence tomography system according to claim 9, wherein said optical probe is attachable and removable from said fiber-optic sensor system.

18. An optical coherence tomography system according to claim 17, wherein said optical probe consists essentially of biocompatible materials that remain undamaged at autoclaving temperatures.

19. An optical coherence tomography system, comprising:
a fiber-optic sensor system;
a light source optically coupled to said fiber-optic sensor system; and
a detection system optically coupled to said fiber-optic sensor system,
wherein said fiber-optic sensor system comprises an optical probe, comprising:
a sheath having a proximal end and a distal end, said sheath defining a lumen therein,
an optical fiber disposed at least partially within said lumen of said sheath, and
a sapphire lens attached to said distal end of said sheath to form a fluid-tight seal to prevent fluid from entering said lumen of said sheath,
wherein said optical fiber has an end arranged in an optical path with said sapphire lens to provide optical coupling between said sapphire lens and said optical fiber,
wherein said end of said optical fiber is fixed within said lumen to maintain a predetermined distance from said sapphire lens with a space reserved therebetween, and
wherein said space is substantially a vacuum such that said end of said optical fiber reflects a portion of illumination light to provide a reference beam to be mixed with received light, said optical coherence tomography system being a common path optical coherence tomography system.

* * * * *